United States Patent
Tee et al.

(10) Patent No.: US 9,848,775 B2
(45) Date of Patent: Dec. 26, 2017

(54) PASSIVE AND WIRELESS PRESSURE SENSOR

(71) Applicant: The Board of Trustees of the Leland Stanford Junior University, Stanford, CA (US)

(72) Inventors: Chee-Keong Tee, Stanford, CA (US); Lisa Yun Chen, San Francisco, CA (US); Zhenan Bao, Stanford, CA (US); Darren Lipomi, San Diego, CA (US); Michael V. McConnell, Stanford, CA (US); H. S. Philip Wong, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 212 days.

(21) Appl. No.: 14/285,495

(22) Filed: May 22, 2014

(65) Prior Publication Data
US 2014/0350348 A1    Nov. 27, 2014

Related U.S. Application Data

(60) Provisional application No. 61/826,376, filed on May 22, 2013.

(51) Int. Cl.
*A61B 5/00* (2006.01)
*G01L 1/14* (2006.01)
(Continued)

(52) U.S. Cl.
CPC .......... *A61B 5/0002* (2013.01); *A61B 5/0031* (2013.01); *A61B 5/02444* (2013.01);
(Continued)

(58) Field of Classification Search
CPC . A61B 5/0031; A61B 5/0215; A61B 2562/02; A61B 2562/0261;
(Continued)

(56) References Cited

U.S. PATENT DOCUMENTS 3,789,325 A * 1/1974 Hoffman ............... H01P 9/003
                                          333/230
5,105,158 A * 4/1992 Fiedziuszko .......... G01R 1/07
                                          324/693
(Continued)

FOREIGN PATENT DOCUMENTS

WO    0000080 A1    1/2000
WO    03073959 A2   9/2003
(Continued)

OTHER PUBLICATIONS

Drazan et al. "Archimedean Spiral Pairs with no Electrical Connections as a Passive Wireless Implantable Sensor". Journal of Biomed. Tech. and Research. Aug. 18, 2014. Accessed Jan. 9, 2017 <http://www.elynsgroup.com/journal/j-biomed-tech-res/article/archimedean-spiral-pairs-with-no-electrical-connections-as-a-passive-wireless-implantable-sensor>.*

(Continued)

*Primary Examiner* — Jonathan Dunlap
(74) *Attorney, Agent, or Firm* — Crawford Maunu PLLC

(57) ABSTRACT

Aspects of the present disclosure are directed to pressure sensing. As may be implemented in accordance with one or more embodiments, an external energy field is applied to a resonant circuit having inductive conductors separated by a compressible dielectric, for wirelessly detecting pressure. Specifically, the resonant circuit is responsive to the energy field and applied pressures by operating in respective states exhibiting different resonant frequencies that are based upon pressure-related compression of the compressible dielectric.

(Continued)

These resonant frequencies, or a change in the resonant frequencies, can be used as an indication of the pressure.

20 Claims, 3 Drawing Sheets

(51) Int. Cl.
| | |
|---|---|
| *A61B 5/024* | (2006.01) |
| *A61B 5/03* | (2006.01) |
| *A61B 5/20* | (2006.01) |
| *G01L 9/12* | (2006.01) |
| *G01L 9/00* | (2006.01) |
| *G01L 9/10* | (2006.01) |

(52) U.S. Cl.
CPC .............. *A61B 5/031* (2013.01); *A61B 5/205* (2013.01); *A61B 5/6847* (2013.01); *A61B 2562/0247* (2013.01); *G01L 1/142* (2013.01); *G01L 1/144* (2013.01); *G01L 1/146* (2013.01); *G01L 9/007* (2013.01); *G01L 9/0072* (2013.01); *G01L 9/10* (2013.01); *G01L 9/12* (2013.01)

(58) Field of Classification Search
CPC ........ A61B 2562/028; A61B 2562/046; G01L 1/142; G01L 1/144; G01L 1/146; G01L 9/007; G01L 9/0072; G01L 9/10; G01L 9/12
USPC ................... 73/780, 774, 777; 600/377, 587
See application file for complete search history.

(56) References Cited

U.S. PATENT DOCUMENTS

| | | | | | |
|---|---|---|---|---|---|
| 5,251,001 | A | * | 10/1993 | Dave | G01M 11/3109 250/227.11 |
| 5,289,435 | A | * | 2/1994 | Milner | B60T 7/20 280/186 |
| 5,610,340 | A | | 3/1997 | Carr | |
| 5,747,698 | A | * | 5/1998 | Spillman, Jr. | G01B 7/22 73/774 |
| 6,025,725 | A | * | 2/2000 | Gershenfeld | H01F 17/0006 324/652 |
| 6,043,644 | A | * | 3/2000 | de Coulon | G01P 3/488 324/164 |
| 6,368,275 | B1 | * | 4/2002 | Sliwa | A61B 5/0031 600/302 |
| 6,466,114 | B1 | * | 10/2002 | Alexandersson | H03J 3/185 333/174 |
| 6,749,568 | B2 | * | 6/2004 | Fleischman | A61B 3/16 600/399 |
| 7,017,419 | B2 | | 3/2006 | Pederson et al. | |
| 7,146,861 | B1 | | 12/2006 | Cook et al. | |
| 7,273,457 | B2 | * | 9/2007 | Penner | A61B 5/00 600/561 |
| 7,444,878 | B1 | * | 11/2008 | Pepples | G01L 9/007 73/722 |
| 7,900,518 | B2 | | 3/2011 | Tai et al. | |
| 8,259,002 | B2 | * | 9/2012 | Vacanti | G01S 7/4008 342/120 |
| 8,831,917 | B2 | * | 9/2014 | Wang | H03H 7/0115 307/104 |
| 9,136,769 | B2 | * | 9/2015 | Schroeder gen Berghegger | H02M 3/33523 |
| 2003/0030994 | A1 | * | 2/2003 | Takaya | H01F 5/06 361/728 |
| 2004/0133092 | A1 | * | 7/2004 | Kain | A61B 5/0031 600/377 |
| 2005/0193818 | A1 | * | 9/2005 | Cobb | G01V 1/005 73/579 |
| 2006/0117859 | A1 | * | 6/2006 | Liu | A61B 5/02152 73/753 |
| 2006/0145697 | A1 | * | 7/2006 | Mikhaltsevitch | G01R 33/441 324/318 |
| 2006/0196276 | A1 | * | 9/2006 | Fortune | G01G 19/4142 73/780 |
| 2006/0196281 | A1 | * | 9/2006 | Koors | G01G 7/06 73/862.626 |
| 2006/0235310 | A1 | * | 10/2006 | O'Brien | A61B 5/0031 600/486 |
| 2008/0015421 | A1 | * | 1/2008 | Penner | A61B 5/00 600/300 |
| 2009/0302841 | A1 | * | 12/2009 | Avdievich | G01R 33/3415 324/309 |
| 2010/0250170 | A1 | * | 9/2010 | Kalinin | B60C 23/0408 702/77 |
| 2011/0152725 | A1 | * | 6/2011 | Demir | A61B 5/0031 600/587 |
| 2012/0075241 | A1 | | 3/2012 | Bao et al. | |
| 2013/0047747 | A1 | * | 2/2013 | Joung, II | G01L 1/142 73/862.68 |
| 2013/0296721 | A1 | * | 11/2013 | Yadav | A61B 5/0031 600/488 |
| 2014/0197694 | A1 | * | 7/2014 | Asanuma | H01F 38/14 307/104 |
| 2014/0243703 | A1 | * | 8/2014 | Schmidt | A61B 5/031 600/561 |
| 2015/0355039 | A1 | * | 12/2015 | Duchaine | G01L 1/146 73/862.046 |

FOREIGN PATENT DOCUMENTS

| | | |
|---|---|---|
| WO | 2008027996 A2 | 3/2008 |
| WO | 2010129446 A1 | 11/2010 |

OTHER PUBLICATIONS

"Fundamentals of Rf and Microwave Power Measurements" Application Note 64-1A, Hewlett-Packard. Jun. 1998. <http://literature.cdn.keysight.com/litweb/pdf/5989-6255EN.pdf?id=919160>.*
"Network Analysis Back to Basics" Agilent Technologies. Sep. 2011. <http://www.keysight.com/upload/cmc_upload/All/NetworkAnalysisBacktoBasics.pdf>.*
Farahman, Farid. "Introduction to Transmission Lines Part II" Fall 2012. <https://www.sonoma.edu/users/f/farahman/sonoma/General_Lectures/TransmissionLines/TransLine/TransmissionLinesPart_II.pdf>.*
Chen, Yun. "Scalable wireless monitoring systems with passive sensors for biomedical applications". Aug. 2013. <http://purl.stanford.edu/sm844rm2546>.*
Nichols, W. W. Clinical measurement of arterial stiffness obtained from noninvasive pressure waveforms. Am. J. Hypertens. 18, 3S-10S (2005).
D. Marioli, E. Sardini, M. Serpelloni, and A. Taroni, "A new measurement method for capacitance transducers in a distance compensated telemetric sensor system," Meas. Sci. Technol., vol. 16, No. 8, pp. 1593-1599, Jun. 2005.
M.G. Allen, "Micromachined endovascularly—implantable wireless aneurysm pressure sensors: from concept to clinic," Proc. 13th I t. Co f. o Solid-States Sensors, Actuators, and Microsystems, Korea, Jun. 2005.
A. Taflove and S.C. Hagness, Computational Electrodynamics— The Finite Difference Time Domain Method, 3rd Ed, Norwood, MA: Artech House Inc., 2005 (1000+ page book) Book Description Included.
Ma. Fonseca, M.G. Allen, J. Kroh, and J. White, "Flexible wireless passive pressure sensors for biomedical applications," in Proc. 12th Solid State Se s. Actuators, Microsyst. Workshop, Hilton Head Island, SC, Jun. 4-8, 2006, pp. 37-42.
M-R. Tofighi, U. Kawoos, F.A. Kralick, a d A. Rose, "Wireless intracranial pressure monitoring through scalp at microwave frequencies; preliminary phantom and animal study," IEEE TT-S Int. Microwave Symp. Digest, San Francisco, CA, pp. 1738-1741, Jun. 2006 Abstract Only.

(56) References Cited

OTHER PUBLICATIONS

Y. Rahmat-Samii and J. Kim, Implanted Antennas in medical wireless communications, Morgan and Claypool Publishers, 2006 Abstract Only.

M. Nabipoor and B.Y. Majlis, "A new passive telemetry LC pressure and temperature sensor optimized for TPMS," J. Phys. Conf. Ser., vol. 34, pp. 770-775, Apr. 2006.

Sajeeda and T.J. Kaiser, "Passive Telemetric Readout System," IEEE Sens. J., vol. 6, No. 5, Oct. 2006 Abstract Only.

Seo, W. S., Lee, J. H., Sun, X., Suzuki, Y., Mann, D., Liu, Z., Terashima, M., Yang, P. C., McConnell, M. V., Nishimura, D.G. & Dai, H. FeCo/graphitic-shell nanocrystals as advanced magnetic-resonance-imaging and near-infrared agents. Nat. Mater. 5, 971-976 (2006). Abstract Only.

B. Guo, J. Li, and H. Zmuda, "A New FDTD Formulation for Wave Propagation in Biological Media with Cole-Cole Model," IEEE Microwave and Wireless Components Letters, vol. 16, No. 12, Dec. 2006. Abstract Only.

Champion, J. A. & Mitragotri, S. Role of target geometry in phagocytosis. Proc. Natl. Acad. Sci. U.S.A. 103, 4930-4934 (2006).

Akin, D., Sturgis, J., Ragheb, K., Sherman, D., Burkholder, K., Robinson, J. P., Bhunia, A. K., Mohammed, S. & Bashir, R. Bacteria-mediated delivery of nanoparticles and cargo into cells. Nat. Nanotechnol. 2, 441-449 (2007).

J. Garcia-Canton, A. Merlos, and A. Baldi, "High-quality factor electrolyte insulator silicon capacitor for wireless chemical sensing," IEEE Electro Device Lett., vol. 28, No. 1, pp. 27-29, Jan. 2007 Abstract Only.

P.-J. Chen, D.C. Rodger, S. Saati, M.S. Humayun, and Y.-C. Tai, "Microfabricated implantable parylene-based wireless passive intraocular pressure sensors," J. Microelectromech. Sys., vol. 17, No. 6, pp. 1342-1351 Dec. 2008.

P.-J.Chen, D.C. Rodger, S. Saati, M.S. Humayun, and Y.-C. Tai, "Implantable parylene-based wireless intraocular pressure sensor," in Proc. 21st IEEE Int. Conf. MEMS, Tuscon, AZ, Jan. 13-17, 2008, pp. 58-61.

F. L. Teixeira, "Time-domain finite-difference and finite-element methods for Maxwell equations in complex media," IEEE Trans. Antennas Propag., vol. 56, o. 8, pp. 2150-2166, Aug. 2008.

Soman, N.R., Marsh, J.N., Lanza, G.M. & Wickline, S.A. New mechanisms for non-porative ultrasound stimulation of cargo delivery to cell cytosol with targeted perfluorocarbon nanoparticles. Nanotechnology 19, 185102 (2008).

Citerio, G., Piper, I., Chambers, I. R., Galli, D., Enblad, P., Kiening, K., Ragauskas, A., Sahuquillo, J. & Gregson, B. Multicenter clinical assessment of the Raumedic Neurovent-P intracranial pressure sensor: a report by the BrianIT group. Neurosurgery 63. 1152-1158 (2008).

Champion, J. A., Walker, A. & Mitragotri, S. Role of particle size in phagocytosis of polymeric microspheres. Pharm. Res. 25, 1815-1821 (2008).

U. Kawoos, R.V. Warty, M-R. Tofighi, F.A. Kralick, a d A. Rosen, "In-vitro and in-vivo trans-scalp evaluation of a intracranial pressure monitoring implant at 2.4," IEEE Trans. Microwave Theory Tech., vol. 56, No. 10, pp. 2356-2365, Oct. 2008. Abstract Only.

K. Takahata and Y.B. Gianchandani, "A micromachined capacitive pressure sensor using a cavity-less structure with bulk-metal/elastomer layers and its wireless telemetry application," Sensors, vol. 8, pp. 2317-2330, 2008.

J.W. Hand, "Modeling the interaction of electromagnetic fields (10-10 GHz) with the human body: methods and applications," Phys. ed. Biol., pp. R243-R286, 53, 2008. Abstract Only.

David A. Sanchez-Hernandez, High Frequency Electromagnetic Dosimetry. Norwod, MA: Artech House Inc., 2009. Book (description and contents provided).

Lin, J., Chen, R., Feng, S., Li, Y., Huang, Z., Xie, S., Yu, Y., Cheng, M. & Zeng, H. Rapid delivery of silver nanoparticles into living cells by electroporation for surface-enhanced Raman spectroscopy. Biosens. Bioelectron. 25, pp. 388-394 (2009). Abstract Only.

Cong, P., Chaimanonart, N., Ko, W. H. & Young, D. J. A wireless and batteryless 130mg 300μm 10b implantable blood-pressure-sensing microsystem for real-time genetically engineered mice monitoring. IEEE ISSCC Dig. Tech. Papers, pp. 428-429 (2009). Abstract Only.

Silasi, G., MacLellan, C. L. & Colbourne, F. Use of telemetry blood pressure transmitters to measure intracranial pressure (ICP) in freely moving rats. Curr. Neurovasc. Res. 6, pp. 62-69 (2009).

Lee, B. & Wong, H-S. P. NiO resistance change memory with a novel structure for 3D integration and improved confinement of conduction path. Proc. Int. Symp. VLSI Techol., pp. 28-29 (2009). Abstract Only.

Fernandez-Rosas, E., Gomez, R., Ibanez, E., Barrios, L., Duch, M., Esteve, J., Nogues, C. & Plaza, J. A. Intracellular polysilicon barcodes for cell tracking. Small 5, pp. 2433-2439 (2009). Abstract Only.

Poon, A. S. Y., O'Driscoll, S. & Meng, T. H. Optimal frequency for wireless power transmission into dispersive tissue. IEEE Trans. Ant. Propag. 58, pp. 1739-1750 (2010).

S.C.B. Mannsfeld, B.C.K. Tee, R. Stoltenberg, C.V.H.H. Chen, S. Barmann, B.V.O. Muir, A.N. Sokolov, C. Reese, Z. Bao, "Highly sensitive flexible pressure sensors with micro-structured rubber as the dielectric layer," Nature Materials, vol. 9, pp. 859-864, 2010. Abstract Only.

Levy, R., Shaheen, U., Cesbron, Y. & See, V. Gold nanoparticles delivery in mammalian live cells: a critical review. Nano Reviews 1, 4889 (2010).

Fernandez-Rosas, E., Gomez, R., Ibanez, E., Barrios, L., Duch, M., Esteve, J., Plaza, J. A. & Nogues, C., Internalization and cytotoxicity analysis of silicon-based microparticles in macrophages and embryos. Biomed. Microdevices 12, 371-379 (2010). Abstract Only.

Gomez-Martinez, R., Vazquez, P., Duch, M., Muriano, A., Pinacho, D., Sanvicens, N., Sanchez-Baeza, F., Boya, P., de la Rosa, E. J., Esteve, J., Suarez, T. & Plaza, J. A. Intracellular silicon chips in living cells. Small 6, 499-502 (2010).

R. Nopper, R. Niekrawiet, and L. Reindl, "Wireless readout of passive LC sensors," IEEE Trans. Instrum. Meas., vol. 59, No. 9, pp. 2450-2457, Sep. 2010. Abstract Only.

P.-J. Chen, S. Saati, R. Varma, M.S. Humayun, and Y.-C. Tai, "Wireless intraocular pressure sensing using microfabricated minimally invasive flexible-coiled LC sensor implant," J. Microelectromech. Sys., vol. 19, No. 4, pp. 721-734, Dec. 2010.

R. Nopper, R. Has, and L. Reindl, "A wireless sensor readout system—circuit concept, simulation, and accuracy," IEEE Trans. Instrum. Meas., vol. 60, No. 8, pp. 2976-2983, Aug. 2011. Abstract Only.

Bohr, M. The evolution of scaling from the homogeneous era to the heterogeneous era. IEEE Int. Elec. Dev. Mtg., 1.1.1-1.1.6 (2011). Abstract Only.

Terashima, M., Uchida, M., Kosuge, H., Tsao, P. S., Young, M. J., Conolly, S. M., Douglas, T. & McConnell, M. V. Human ferritin cages for imaging vascular macrophages. Biomaterials 32, 1430-1437 (2011).

A. Garrison Darrin and R. Osiander, MEMS Materials and Processes Handbook, Chapter 12, Springer Science+Business Media, New York, NY, 2011. Book Preface & Contents Only.

Chen, G., Ghaed, H., Haque, R., Wieckowski, M., Kim, Y., Kim, G., Fick, D., Kim, D., Seok, M., Wise, K., Blaauw, D. & Sylvester, D. A cubic-millimeter energy-autonomous wireless intraocular pressure monitor. IEEE ISSCC Dig. Tech. Papers, 310-311 (2011).

M.M. Jatlaoui, F. Chebila, P. Pons, and H. Aubert, "Working principle descriptionof the wireless passive EM transduction pressure sensor," Eur. Phys. J. Appl. Phys., vol. 56, No. 1, pp. 13702, Oct. 2011.

A. Bell, "A resonance approach to cochlea mechanics," PLoS ONE, vol. 7, No. 11, pp. e47918, 2012.

X. Meng, K.D. Brown, S-M. Huang, C. Mietus, D.K. Cullen, M-R. Tofighi, "Dynamic evaluation of a digital wireless intracranial pressure sensor for the assessment of traumatic brain injury in a swine model," IEEE Trans. Microwave Theory Tech., vol. 61, No. 1, pp. 316-325, 2012.

Cheong, J. H., Ng, S. S. Y., Liu, X., Xue, R-F., Lim, H. J., Khannur, P. B., Chan, K. L., Lee, A. A., Kang, K., Lim, L. S., He, C., Singh,

(56) References Cited

OTHER PUBLICATIONS

P., Park, W-T. & Je, M. An inductively powered implantable blood flow sensor microsystem for vascular grafts. IEEE Trans. Biomed. Eng. 59. 2466-2475 (2012). Abstract Only.

Orakcioglu, B., Beynon, C., Kentar, M, M., Eymann, R., Kiefer, M. & Sakowitz, O. W. Intracranial pressure telemetry: first experience of an experimental in vivo study using a new device. Acta Neurochir. Suppl. 114. 105-110 (2012). Book Abstract Only.

Kiefer, M., Antes, S., Leonhardt, S., Schmitt, M., Orakcioglu, B., Sakowitz, O.W. & Eymann, R. Telemetric ICP measurement with the first CE-approved device: data from animal experiments and initial clinical experiences. Acta Neurochir. Suppl. 114. 111-116 (2012). Abstract Only.

Kim, S., Ho, J. S., Chen, L.Y. & Poon, A. S. Y. Wireless power transfer to a cardiac implant. Appl. Phys. Lett. 101, 073702 (2012).

P.H. Raboel, J. Bartek Jr., M. Andresen, B.M. Bella der, a d B. Romner, "Intracranial pressure monitoring: invasive versus non-invasive methods—a review," Critical Care Research and Practice, pp. 950393, 2012.

S-H. Song, G.T. Gilles, M.R. Begley, M. Utz, and W.C. Broaddus, "Inductively coupled microfluidic pressure meter for in vivo monitoring of cerebrospinal fluid shunt function," J. Med. Eng. Tech. vol. 36, No. 3, pp. 156-162, 2012. Abstract Only.

H.A. Wheeler, "Simple inductance formulas for radio coils," Proc. IRE, Oct. 1928, vol. 16, No. 10, pp. 1398-1400. First Page Only R.S. Mackay and B. Jacobson, "Endoradiosonde," Nature, vol. 179, pp. 1239-1240, 1957. Abstract Only.

J.T. Farrar and V.K. Zworykin, "Telemetering of gastrointestinal pressure in man by means of an intraluminal capsule energized from an external wireless source," The Physiologist, vol. 2, p. 37, Aug. 1959.

R.S. Mackay, "Endoradiosondes: further notes," IRE Trans. on Medical Electronics, vol. ME-7, pp. 67-73, Jan. 1960.

Vaheri, A. & Pagano, J. S. Infectious poliovirus RNA: A sensitive method of assay. Virology 27, 434-436 (1965). First Page Only C.C. Collins, "Miniature passive pressure transensor for implanting in the eye," IEEE Trans. Biomed. Eng., vol. BME-14, No. 2, pp. 74-83, Apr. 1967. Abstract Only.

Olsen, E. R., Collins, C. C., Loughborough, W. F., Richards, V., Adams, J. E. & Pinto, D. W. Intracranial pressure measurement with a miniature passive implanted pressure transensor. Am. J. Surg. 113. 727-729 (1967). Abstract Only.

Atkinson, J. R., Shurtleff, B. & Foltz, E. L. Radio telemetry for the measurement of intracranial pressure. J. Neurosurg. 27, 428-432 (1967).

McCutchan, J. H. & Pagano, J. S. Enhancement of the infectivity of simian virus 40 deoxyribonucleic acid with diethylaminoethyl-dextran. J. Natl. Cancer Inst. 41, 351-357 (1968). Abstract Only.

Graham, F. L. & van der Eb, A. J. A new technique for the assay of infectivity of human adenovirus 5 DNA. Virology 52, 456-67 (1973). Abstract Only.

Hanna, F. F., Yehia A. A., & Abou-Bakr, A.-F., Dielectric Properties of Styrene-Butadiene Rubber/Silicon Dioxide Mixtures. Br. Polym. J. 5, pp. 83-90, 1973. Abstract Only.

De Jong, D. A., den Ouden, A. H., van de Boon, A., Eyskoot, F. & Maas, A. I. R. Telemetred epidural pressure. Biotelemetry 2. 257-64 (1975). Abstract Only.

Zervas, N. T., Cosman, E. R. & Cosman, B. J. A pressure-balanced radio-telemetry system for the measurement of intracranial pressure. J. Neurosurg. 47. 899-911 (1977). Abstract Only.

De Jong, D. A., Berfelo, M. W., de Lange, S. A. & Maas, A. I. R. Epidural pressure monitoring with the so-called Rotterdam transducer. Further in Vivo Results. Acta Neurochir 45, 301-309 (1979). Abstract Only.

Maas, A. I. R. & De Jong, D. A. The Rotterdam teletransducer: state of the device. Acta Neurochir. 79, 5-12 (1986). Abstract Only.

E. M. Schmidt, J. S. McIntosh, M. J. Bak, Long-term implants of Parylene-C coated microelectrodes, Med. Biol. Eng. Computing, vol. 26, pp. 96-101, 1988.

Hall, J. B., Schmidt, G. A. & Wood, L. D. H (Eds.). Principles of critical care (McGraw-Hill, New York, 1992). Book, Full Copy Unavailable (Table of Contents included).

W. Sui, D.A. Christensen and C. H. Durney, "Extending the Two-Dimensional FDTD Method to Hybrid Electromagnetic Systems with Active and Passive Lumped Elements," IEEE Trans on Microwave Theory Tech., vol. 40, No. 4, pp. 724-730, Apr. 1992. Abstract Only.

L. Rosengren, Y. Backlund, T. Sjostrom, B. Hok, and B. Svedbergh, "A system for wireless intraocular pressure measurements using a silicon micromachined sensor," J. Micromech. Microeng., vol. 2, pp. 202-204, 1992. Abstract Only.

Wayenberg, J.-L., Raftopoulos, C., Vermeylen, D. & Pardou, A. Non-invasive measurement of intracranial pressure in the newborn and the infant: the Rotterdam teletransducer. Arch. Dis. Child 69. 493-497 (1993).

K.S. Kunz and R.J. Luebbers, The Finite Difference Time Domain Method for Electromagnetics, Boca, Raton, FL: CRC Press, 1993. Copy Not Available (464 page book).

L. Rosengren, P. Rangsten, Y. Backlund, B. Hok, B. Svedbergh, and G. Selen, "A system for passive implantable pressure sensors," Sens. Acutators A, Phys., vol. 43, No. 1-3, pp. 55-58, May 1994. Abstract Only.

I.G. Zubal, C.R. Harrell, E.O. Smith, Z. Rattner, G. Gindi, P.B. Hoffer, "Computerized three-dimensional segmented human anatomy," Med. Phys., vol. 21, o. 2, pp. 299-302, Feb. 1994.

Peters, R. J. A., Hanlo, P. W., Gooskens, R. H. J. M., Braun, K. P. J., Tulleken, C. A. F. & Willemse, J. Non-invasive ICP monitoring in infants: the Rotterdam teletransducer revisited. Child's Nerv. Syst. 11. 207-213 (1995). Abstract Only.

R. Leubbers and R. Baurle, "FDTD predictions of Electromagnetic Fields in and near Human Bodies using Visible Human Project Anatomical scans," IEEE AP-S Int. Symp. URSI Radio Science Meeting, Baltimore, MD, Jul. 1996. Abstract Only.

Gonzalez, O., Smith, R. L. & Goodman, S. B. Effect of size, concentration, surface area, and volume of polymethylmethacrylate particles on human macrophages in vitro. J. Biomed. Mater. Res. 30, 463-473 (1996). Abstract Only.

J. Hilland, "Simple Sensor System for Measuring the Dielectric Properties of Saline Solutions," Meas. Sci. Technol., vol. 8, pp. 901-910, 1997. Abstract Only.

E. Brown, "Intracranial Pressure Monitoring Devices," Arlington, CA, Association for the Advancement of Medical Instrumentation, 1988.

E-C. Park, J-B Yoon, and E. Yoon, "Hermetically sealed inductor-capacitor (LC) resonator for remote pressure monitoring," Jpn. J. Applied Physics, vol. 37, No. 12b, pp. 7124-7128, Dec. 1998. Abstract Only.

Mohan, S. S., Hershenson, M. D. M., Boyd, S. P. & Lee, T. H. Simple accurate expressions for planar spiral inductances. IEEE J. Solid-State Cir. 34. 1419-1424 (1999).

J.M. English and M.G. Allen, "Wireless Micromachined Ceramic Pressure Sensors," Proc. IEEE Int. Conf. on Micro Electro Mechanical Systems, E S '99, pp. 511-516, Orlando, Florida, Jan. 17-21, 1999.

J. A. Roden and S. D. Gedney, "Convolutional PML (CPML): An Efficient FDTD Implementation of the CFS-PML for Arbitrary Media." Microwave and Optical Technology Letters, Jun. 2000.

A. Pohl, "A Review of Wireless SAW Sensors," IEEE Trans Ultrasonics, Ferroelectrics, and Frequency Control, vol. 47, No. 2, Mar. 2000. Abstract Only.

T. Eggers, C. Marschner, U. Marschner, B. Clasbrummel, R. Laur, J. Bi der, "Advanced hybrid integrated low-power telemetric pressure monitoring systems for biomedical applications," Proc. IEEE MEMS, pp. 329-334, 2000. Abstract Only.

K. G. Ong, C.A. Grimes, "A resonant printed-circuit sensor for remote query monitoring of environmental parameters," Smart Mater. Struc., vol. 9, No. 4 pp. 421-428, Aug. 2000 Abstract Only.

K. G. Ong, C.A. Grimes, C.L. Robbins, and R.S. Singh, "Design and application of a wireless, passive, resonant-circuit environmental monitoring sensor," Sens. Actuators A, Phys., vol. 93, No. 1, pp. 33-43, Aug. 2001 Abstract Only.

(56) References Cited

OTHER PUBLICATIONS

S.Y. Kim, H.J. Kim, J.S. Park, and S.S. Yang, "A telemetry silicon pressure sensor of LC resonance type," Proc. SPIE—Design, Test, Integration and Packaging of MEMS/MOEMS, 2001, pp. 452-462. Abstract Only.

P. Gajsek, W.D. Hurt, H.M. Ziriax, and P.A. Mason, "Parametric Dependence of SAR on Permittivity Values in a Man Model," IEEE Transactions on Biomedical Engineering, vol. 48, No. 10, Oct. 2001 Abstract Only.

M.A. Fonseca, J.M. English, M. von Arx, and M.G. Allen, "High temperature characterization of ceramic pressure sensors," Proc. Transducers 2001, vol. 1, pp. 486-489.

O. Akar, T. Akin, and K. Najafi, "A wireless batch sealed absolute capacitive pressure sensor," Sens. Actuators A, Phys., vol. 95, No. 1, pp. 29-38, Dec. 2001.

M.A. Fonseca, J.M. English, M. von Arx, and M.G. Allen, "Wireless miromachined ceramic pressure sensor for high-temperature applications," J. Microelectromech. Syst., vol. 11, No. 4, pp. 337-343, Aug. 2002.

T. J. Harpster, S. Hauvespre, M.R. Dokmeci, and K. Najafi, "A passive humidity monitoring system for in situ remote wireless testing of micropackages," J. Microelectromech. Syst., vol. 11, No. 1, pp. 61-67, Feb. 2002 Abstract Only.

A. DeHeennis and K.D. Wise, "A double-sided single-chip wireless pressure sensor," in Proc. 15th IEEE Int. Conf. MEMS, Las Vegas, NV, Jan. 20-24, 2002, pp. 252-255.

J.C. Butler, A.J. Vigliotti, F.W. Verdi, and S.M. Walsh, "Wireless, passive, resonant-circuit, inductively coupled, inductive strain senor," Sens. Acutators A, Phys., vol. 102, No. 1/2, pp. 61-66, Dec. 2002 Abstract Only.

Baldi, A., Choi, W. & Ziaie, B. A self-resonant frequency-modulated micromachined passive pressure transenser. IEEE Sensors J. 3. 728-733 (2003). Abstract Only.

K. Takahata, A. DeHennis, K.D. Wise, and Y.B. Gianchandani, "Stentenna: a micromachined antenna stent for wireless monitoring of implantable microsensors," Proc. Int. Conf. IEEE Eng. Med. Biol. Soc., pp. 3360-3363, Cancun, Mexico, Sep. 2003.

Citerio, G., Piper, I., Cormio, M., Galli, D., Cazzaniga, S., Enblad, P., Nilsson, P., Contant, C. & Chambers, I. Bench test assessment of the new Raumedic Neurovent-P ICP sensor: a technical report by the BrianIT group. Acta Neurochir. 146. 1221-1226 (2004).

M. Czosnyka and J.D. Pickard, "Monitoring and interpretation of intracranial pressure," J. Neurol Neurosurg Psychiatry, vol. 75, pp. 813-821, 2004.

J. Coosemans, M. Catrysse, and R. Puers, "A readout circuit for a intraocular pressure sensor," Sens. Actuators A, Phys., vol. 110, No. 1-3, pp. 432-438, Feb. 2004 Abstract Only.

H. J. Yoon, J.M. Jung, J.S. Jeong, and S.S. Yang, "Micro devices for a cerebrospinal fluid (CSF) shunt system," Sens. Actuators A, Phys., vol. 110, No. 1-3, pp. 68-76, Feb. 2004.

J. Jeon, H.B. Lee, Z. Bao, Flexible Wireless Temperature Sensors Based on Ni Microparticle-Filled Binary Polymer Composites, Adv. Mater., 25, 850-855, 2013 Abstract Only.

G.Chitnis, T. Maleki, B. Samuels, L.B. Cantor, and B. Ziaie, "A minimally invasive implantable wireless pressure sensor for continuous IOP monitoring," IEEE Trans. Biomed. Eng., vol. 60, No. 1, Jan. 2013 Abstract Only.

M.-H. Tsai, C.-J. Chang, H.-H. Lu, Y.-F. Liao, I-H. Tseng, Properties of Magnetron Sputtered Moisture Barrier layer on transparent polyimide/graphene nanocomposite film, Thin Solid Films, vol. 544, pp. 324-330, 2013 Abstract Only.

S. Kirsten, J. Wetterling, J. Uhlemann, K. Wolter, S. Zigler, Barrier Properties of Polymer Encapsulation Materials for Implantable Microsystems, IEEE Int. Conf. Elect. Nanotech. pp. 269-272, 2013 Abstract Only.

C. Gabriel and S. Gabriel, "Compilation of the dielectric properties of body tissues at RF and microwave frequencies," Armstrong Laboratory, London, UK, Available at: http://www.brooks.af.mil/AFRL/HED/hedr/reports/dielectric/home.html.

* cited by examiner

PASSIVE AND WIRELESS PRESSURE SENSOR

FIELD

Aspects of the present disclosure are directed to sensors, and more particularly to passive and wireless pressure sensors.

BACKGROUND

Monitoring physiological variables such as pressure, pH, oxygen level and glucose is useful for routine biomedical research and clinical practice. Patients in critical care units are typically monitored at regular intervals, and often continuously, so that medical staff can track their physiologic status in real time. However, continuous monitoring of these physiological parameters often requires tethered, wired connections. For example, use of an implanted catheter with an external transducer is standard for monitoring intracranial pressure (ICP) in patients suffering from head trauma. The ability to assess intracranial hypertension continuously is important for prompting intervention and achieving favorable outcomes. However, tethered solutions cause patient discomfort and carry a risk of infection and complications stemming from dislodgement, leakage and blockage.

Passive (non-tethered) solutions have included low frequency approaches, which may require relatively large components and translate to a sensor size in the $cm^3$ range. Wireless solutions, such as those for ICP monitoring, may also involve large sizes, as they use batteries and active circuitry to power the sensor device. Further, while integrated circuit (IC) chip size can be relatively small for actively powered wireless pressure devices, these devices generally require additional space for a separate antenna coil. Further, certain passive strategies have been limited by self-resonant frequencies of readout circuitry, as interference effects make it difficult to detect sensors operating near and above this frequency. These and other matters have presented challenges to various sensor applications.

SUMMARY

Aspects of the present disclosure are believed to be applicable to a variety of different types of devices, systems and arrangements, including those involving wireless monitoring of in vivo properties such as biopotential, biochemical and biomechanical. Monitoring of various in vivo properties allows, for example, understanding of human health and disease. Monitoring these properties on a cellular level, as in the present disclosure, allows for greater scaleable and accurate sensors. Various aspects of the present disclosure utilize a passive approach of wireless detection to individually address and continuously monitor implantable sensors.

In accordance with another embodiment, an external energy field is applied to a resonant circuit having inductive conductors separated by a compressible dielectric that supports the inductive conductors. Energy from the external energy field is used for wirelessly detecting pressure applied to the compressible dielectric by operating the resonant circuit respective states in which the resonant circuit exhibits different resonance in response to different pressures applied in each state. The pressure is detected based on the resonance.

Another embodiment is directed to an apparatus having a resonant circuit with inductive conductors, and a compressible dielectric that supports the inductive conductors, and that compresses and expands in response to changes in pressure. The compressible dielectric operates with the inductive conductors to provide a first state in which the compressible dielectric is in a first state of compression corresponding to a first pressure applied to the compressible dielectric, and in a second state in which the compressible dielectric is in a second state of compression corresponding to a second pressure that is different than the first pressure applied to the compressible dielectric. The resonant circuit exhibits a first resonant frequency in response to an external energy field in the first state, with the first resonant frequency being based upon the first pressure. The resonant circuit exhibits a second resonant frequency in response to the external energy field, with the second resonant frequency being based upon the second pressure and being different than the first resonant frequency.

Another embodiment is directed to an apparatus having a resonant circuit with first and second inductive coils separated by a structured elastomeric dielectric layer. The dielectric layer has microstructures that define gap regions and is operable to exhibit a changed dielectric constant of the structured elastomeric dielectric layer in response to applied pressure (e.g., and compression/shaping of the microstructures). At least one of the inductive coils receives wireless energy, and the first and second inductive coils use the wireless energy to exhibit a resonant frequency that varies in response to changes in the dielectric constant (e.g., the effective dielectric constant) due to the applied pressure. The first and second inductive coils are configured and arranged to use the wireless energy to transmit a wireless signal that is based upon the dielectric constant and indicative of the applied pressure (e.g., by reflecting energy based on resonance).

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1:
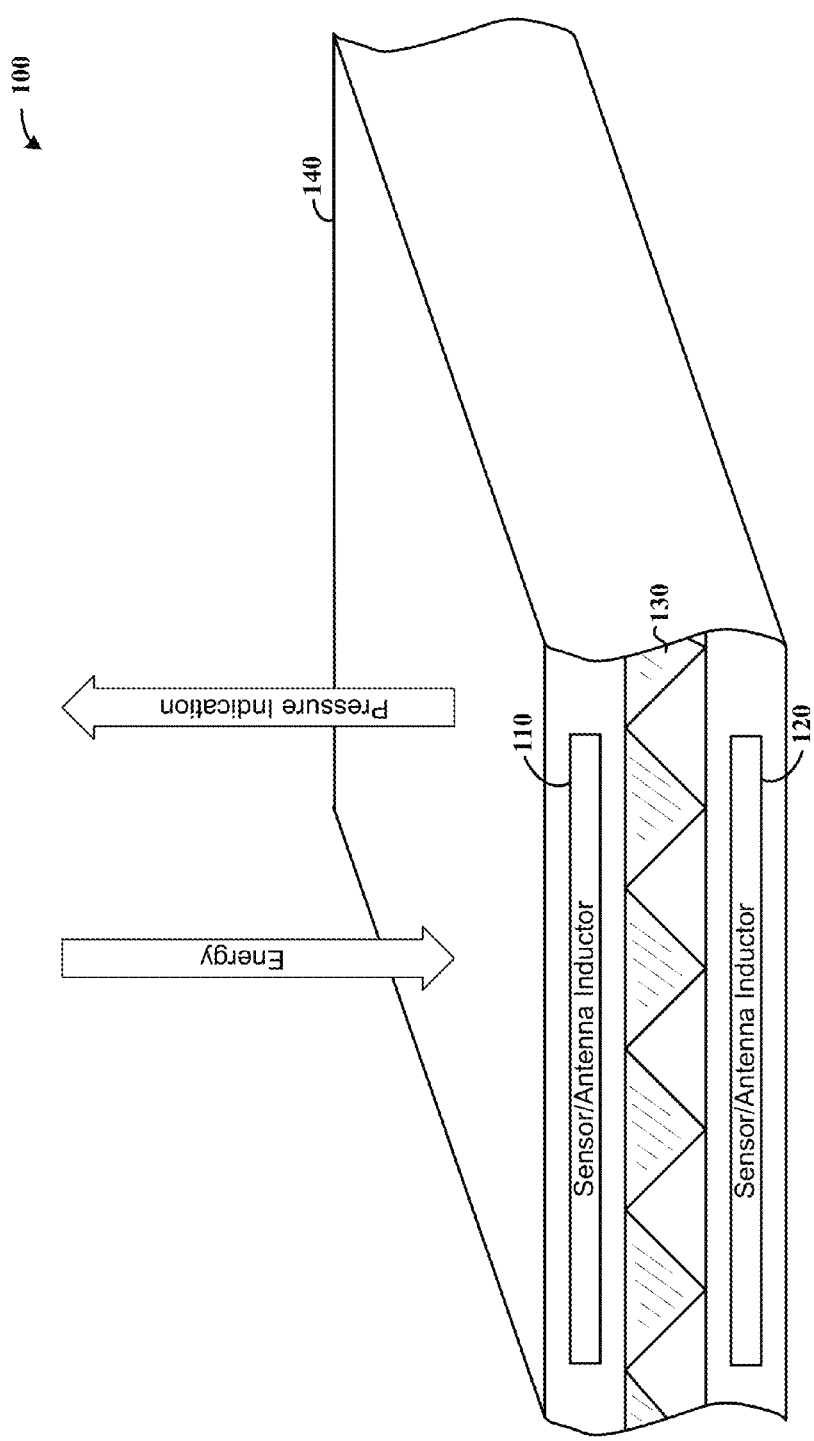
FIG. 1 shows a pressure sensor apparatus, in accordance with an example embodiment.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims.

DESCRIPTION

Various aspects of the present disclosure are directed toward passive implantable pressure sensors. In certain embodiments, the sensors include inductive coils that sandwich a micro-structured elastomeric dielectric layer. Aspects of the present disclosure utilizing the micro-structured elastomeric dielectric layer increase capacitance change, and as a result, lowers the frequency of the implantable sensor to GHz frequencies despite its small dimensions. In certain embodiments, the frequency of the sensor is inversely related to the length of the inductor coils and capacitance created in response to pressure by the coils and the micro-structured elastomeric dielectric layer.

In certain embodiments, the micro-structured elastomeric dielectric layer is coupled to an inductive coil to form a resonant LC tank circuit. In such embodiments, as the pressure increases, the resonant frequency of the circuit decreases. The sensor can be implanted into a patient, and in order to receive the resonant frequencies produced in response to pressure, a small antenna coil (e.g., a receiver) can be oriented outside of the patient, and near the region of the implanted sensor to detect the change in frequency.

Surprisingly, the scaled-down sensor, consistent with various aspects of the present disclosure, can be passively and wirelessly detected even with the higher resonant frequencies that result from smaller-sized sensors. Thus, various aspects of the present disclosure are directed toward increasing operating frequencies as the sensor size is scaled down. As a particular example, and as discussed in detail in Chapters 2 and 4 of Appendix A in underlying U.S. Provisional Patent Application Ser. No. 61/826,376 (to which benefit is claimed), utilizing group delay distortions (GDD) allows for sensor operation in high frequency regimes (above the readout circuit self-resonance). More specifically, the resonant frequency of an implantable sensor, consistent with various aspects of the present disclosure, is identified by searching for the maximum GDD over an input frequency range.

Various aspects of the present disclosure are directed towards apparatus and methods that include a structured microstructured-dielectric layer and a resonant LC tank circuit. The resonant LC tank circuit has opposing coil structures that are provided on an opposing side of the structured microstructured dielectric layer. The resonant LC tank circuit is provided as an inductive spiral adjacent a diaphragm layer having a structured elastomeric dielectric. The structured elastomeric dielectric layer has at least one undulating side facing one of the coil structures. Additionally, in response to pressure applied relative to one side of the structured microstructured dielectric layer, the resonant frequency of the resonant LC tank circuit changes due to a response in the diaphragm layer. The structured microstructured-dielectric layer and the resonant LC tank circuit are secured in a housing structure, which is sized for implantation and passive wireless transmission of signals in response to the changes of the resonant frequency of the resonant LC tank circuit.

In certain embodiments, the apparatus or methods of the present disclosure include a housing structure that deforms according to the pressure applied relative to one side of the structured microstructured dielectric layer. In this manner, the deformation causes an impedance change associated with the dielectric layer and the resonant LC tank circuit. Further, in certain embodiments, the housing structure provides protection from an exterior biological environment. Additionally, certain embodiments of the apparatus or methods of the present disclosure utilize a receiver circuit (including an antenna) to wirelessly detect and receive signals at the transmitted (e.g., resonant) frequency of the resonant LC tank circuit. In such an embodiment, the frequency of the emission is inversely related to the pressure exerted on the sensor by an external force. Moreover, the undulating side of the structured elastomeric dielectric layer includes conical shapes with peaks facing one side of the coil structures.

Certain embodiments of the apparatus or methods of the present disclosure also include a receiver circuit that utilizes GDD to receive and detect the passive wireless transmission of signals in response to the changes of the resonant frequency of the resonant LC tank circuit.

Various aspects of the present disclosure are directed toward pressure sensors provided in intra-cranial applications. In this manner, real-time knowledge of pressure can be used to determine treatment and the best course of action, for example, in brain trauma patients. Additionally, another intra-cranial application includes pressure monitoring to provide a feedback loop for drainage systems to maintain constant intra-cranial pressures. Further, the pressure sensors, consistent with various aspects of the present disclosure, can also be used to diagnose bladder disorders. For instance, the sensors can provide continuous monitoring of bladder pressure during normal (e.g., ambulatory) physiological conditions and/or over several days to capture symptomatic events.

The embodiments and specific applications discussed herein (and in the above-referenced provisional patent application) may be implemented in connection with one or more of the above-described aspects, embodiments and implementations, as well as with those shown in the figures. For instance, as discussed in detail in Chapter 4 of Appendix A of the provisional application, various embodiments are directed to a micro-structured elastomeric dielectric layer that transduces pressure to a capacitance change. This capacitance change causes the coil to resonate at different frequencies depending on the capacitance change. Such aspects may be implemented with one or more embodiments as discussed herein.

The resonance aspects implemented with inductors as described herein can be implemented using one or more of a variety of approaches. In some embodiments, a pressure-sensitive capacitive component is integrated with an inductive antenna to form a resonant circuit that has a unique resonant frequency under zero pressure, and which changes with pressure. A distributed resonant tank is built by stacking a deformable dielectric layer between two such inductive spirals in a sandwich structure. Under applied pressure, separation distance between the spiral layers is reduced, increasing the effective coupling capacitance and shifting the resonant frequency down to lower frequencies. This pressure may further alter dielectric characteristics of the deformable dielectric layer, which may also shift the resonant frequency. This shift is detectable via interaction between the inductive antenna and a communication path (e.g., an electromagnetic field) with a remote reader.

In some embodiments, the spiral layers are printed or lithographically patterned on flexible substrates such as polyimide substrates, and the pressure-sensitive dielectric layer is implemented with a micro-structured dielectric material such as a styrene-butadiene-styrene (SBS) elastomer. In some implementations, the dielectric layer exhibits viscoelastic behavior and changes in effective permittivity under compression, presenting changes in effective permittivity (or dielectric constant) that are in addition to the change in separation distance. In some embodiments, the dielectric layer includes pyramidal elastomer microstructures that deform to fill in air gaps with applied pressure, thus increasing effective permittivity. Such an approach may be implemented using a low-cost wax printing process that may avoid the use of vias or similar connectors for connecting discrete inductive and capacitive structures in parallel.

Wireless operation is achieved through energy field coupling, such as near-field electromagnetic coupling, between the resonant sensor device and an external antenna. In some embodiments, the external antenna is connected to a continuous wave (CW) readout system. In certain implementations, variable frequency CW source generation, incident and reflected wave isolation capabilities of a vector network analyzer (VNA) are used to provide power to and readout information from the sensor. Such a VNA may, for example, be controlled by a Matlab program and connected to the readout antenna through a flexible cable.

In some embodiments, a readout system detects and characterizes one or more sensors by searching for peak power reflection changes over a captured input frequency spectrum. A power reflection distortion (PRD) quantity can be defined as follows, as the function of input reflection coefficients with and without a resonant sensor present:

$$PRD(\omega) = |\Gamma_{in}(\omega)|^2 |_{without\,sensor} - |\Gamma_{in}(\omega)|^2 |_{with\,sensor}. \quad (4)$$

The input reflection is minimal near the sensor resonant frequency when power is maximally absorbed by a resonating sensor. This maximum in the PRD spectrum may occur close to the sensor resonant frequency within a small error that varies inversely with the square of the sensor quality factor $Q_{sensor}$, as:

$$\operatorname*{argmax}_{\omega}[PRD(\omega)] \approx \left(1 + \frac{1}{4Q_{sensor}^2}\right)\omega_{sensor}. \quad (6)$$

In some embodiments, effects relating to power absorption that are media dependent and sensitive to lossy environments such as human tissue can be mitigated, by searching for a greatest change in reflection group delay with a software maximum function. The reflection group delay is found by differentiating the phase response of a system with respect to frequency. A GDD quantity to be the following function of the complex-valued input reflection coefficients $\Gamma_{in}$ with and without a resonant sensor present, $$GDD(w) = \frac{\partial \angle \Gamma_{in}}{\partial w}\bigg|_{without\,sensor} - \frac{\partial \angle \Gamma_{in}}{\partial w}\bigg|_{with\,sensor}. \quad (5)$$

The difference in group delay may be maximal near the sensor resonant frequency within a small error, which varies with the inverse square of the sensor quality factor, as follows:

$$\operatorname*{argmax}_{\omega} GDD(\omega) \approx \left(1 + \frac{1}{8Q_{sensor}^2}\right)\omega_{sensor}. \quad (7)$$

These characteristics are used in accordance with one or more embodiments, for reading a response for one or more sensors as characterized herein.

In some implementations, a readout system as discussed herein is calibrated to determine a reference spectrum in the absence of a sensor, as well as a baseline noise level. In one embodiment, the sensor resonance is detected by triggering excitation over a linear sweep and a fixed frequency range, and a resultant input reflection spectrum is captured. An averaged sequence of these reflection spectrums is taken and a median filter is applied to remove white noise. The measured input reflection spectrum is squared in software and subtracted by the square of the reference spectrum to generate the PRD spectrum. The GDD spectrum is similarly derived from the first derivative of measured input reflection and reference spectrums in software. In a continuous monitoring embodiment, resonant peak detection is run in a loop while rejecting peaks that fail to meet a signal-to-noise ratio (SNR) threshold of 3 dB. In array monitoring, multiple peaks are distinguished by dividing the spectrum into frequency bands based on a SNR threshold.

Another example embodiment is directed to a method in which an external energy field is applied to a resonant circuit having inductive conductors separated by a compressible dielectric that supports the inductive conductors. Energy from the external energy field is used for wirelessly detecting pressure applied to the compressible dielectric by operating the resonant circuit's respective states in which the resonant circuit exhibits different resonance in response to different pressures applied in each state. The pressure is detected based on the resonance (e.g., by using characteristics of the compressible dielectric to alter the resonant frequency of the inductive conductors).

In a particular implementation, the resonant circuit is operated in a first state in which the compressible dielectric is in a first state of compression corresponding to a first pressure applied to the compressible dielectric, and exhibits a first resonant frequency (that is based upon the first pressure) in response to the external energy field. The resonant circuit is operated in a second state in which the compressible dielectric is in a second state of compression corresponding to a second pressure that is different than the first pressure and applied to the compressible dielectric. The resonant circuit exhibits a second resonant frequency in response to the external energy field, with the second resonant frequency being based upon the second pressure and being different than the first resonant frequency.

In some embodiments, the resonant circuit is implanted in a live being, and operated therein by applying the external energy field thereto (such as an electromagnetic field). Pressure changes within the live being are monitored by detecting frequency characteristics of the energy field that are responsive to the resonant frequency of the resonant circuit (e.g., reflection). A value of the resonant frequency can be used to determine a specific pressure, and changes in the resonant frequency can be used as an indication of the pressure changes.

Characteristics of applied pressure are detected by detecting characteristics of the energy field, in a variety of manners. In some embodiments, peak power reflection changes are detected over a captured input frequency spectrum, and a resonant frequency of the resonant circuit is detected based on a maximum in a power reflection distortion spectrum. In other embodiments, a change or changes in reflection group delay are used to identify a resonant frequency, based on a maximum of the group delay distortion over an input frequency range.

While embodiments described herein refer to the use of a sensor, many embodiments involve using two or more such sensors, in which each sensor may have a different resonant frequency at a common pressure. The sensors may, for example, be applied in different locations and used to map pressure by detecting responses of the sensors using the respective resonant frequencies to correlate each response with a specific sensor.

Another embodiment is directed to an apparatus having a resonant circuit with inductive conductors separated by a compressible dielectric that supports the inductive conductors. The apparatus compresses and expands in response to changes in pressure, with the inductive conductors providing resonance in respective states corresponding to the pressure or pressure changes (e.g., exhibiting an impedance change in response to compression of the compressible dielectric). Each state involves compression of the compressible dielectric that corresponds to a pressure applied thereto, with the resonant circuit operating at a resonant frequency that is based upon the applied pressure and specific to each pressure, and an applied energy field (e.g., via near-field electromagnetic coupling, which may provide a detectable interaction with the resonant circuit).

The inductive conductors may be implemented in one or more of a variety of manners. In some embodiments, the conductors include spiral resonators separated by the compressible dielectric and which form a resonant tank structure that exhibits a resonant frequency based upon a state of compression of the compressible dielectric. The resonant frequency can thus be based upon, and used as an indication of, the applied pressure. In some implementations, such spiral resonators rotate in opposite directions in response to the compression or expansion of the compressible dielectric.

The compressible dielectric may be implemented in one or more of a variety of manners. In some embodiments, the compressible dielectric includes a microstructured dielectric having at least one undulating side (e.g., with a surface exhibiting peaks and valleys). A variety of such shapes, such as shown in the figures, may be used. For general information regarding compressible dielectrics, and for specific information regarding compressible dielectrics that may be implemented in connection with one or more embodiments, reference may be made to U.S. Patent Publication No. 2012/0075241 (U.S. Pat. No. 9,112,058) (to Bao, et al.), which is fully incorporated herein by reference.

Turning now to the figures, FIG. 1 shows a pressure sensor apparatus 100, in accordance with another example embodiment. The apparatus 100 includes respective sensor/antenna inductors 110 and 120, separated from one another by a compressible dielectric 130. By way of example, the inductors and dielectric are shown in a housing type structure 140, with the dielectric integrated with/supporting the inductors. In response to an energy field, such as a magnetic field, collected by one or both of the inductors 110 and 120, the inductors operate in accordance with a resonant frequency that is based upon a degree of compression (or lack thereof) of the compressible dielectric 130. For instance, the compressible dielectric 130 is shown with microstructured portions (shown in a triangular shape, by way of example) with gaps therein, and compress relative to the material that forms the microstructured portions and the gaps. The resulting effective dielectric constant operates to set a resonant frequency of the inductors 110 and 120, which is detected as an affect upon and/or other communication via the energy field to provide an indication of pressure.

Various aspects of the apparatus 100 may be implemented in connection with one or more embodiments herein, and many variations may be made thereto. For instance, the positioning of the inductors 110 and 120 can be varied, such as to directly interface with the compressible dielectric 130. In addition, various shapes of the compressible dielectric 130 can be implemented to suit particular embodiments. Further, the arrangement of the housing, and materials used therein, can be tailored to provide desirable pressure-responsive characteristics, such as to tune pressure sensing to a particular range.

Figure 2:
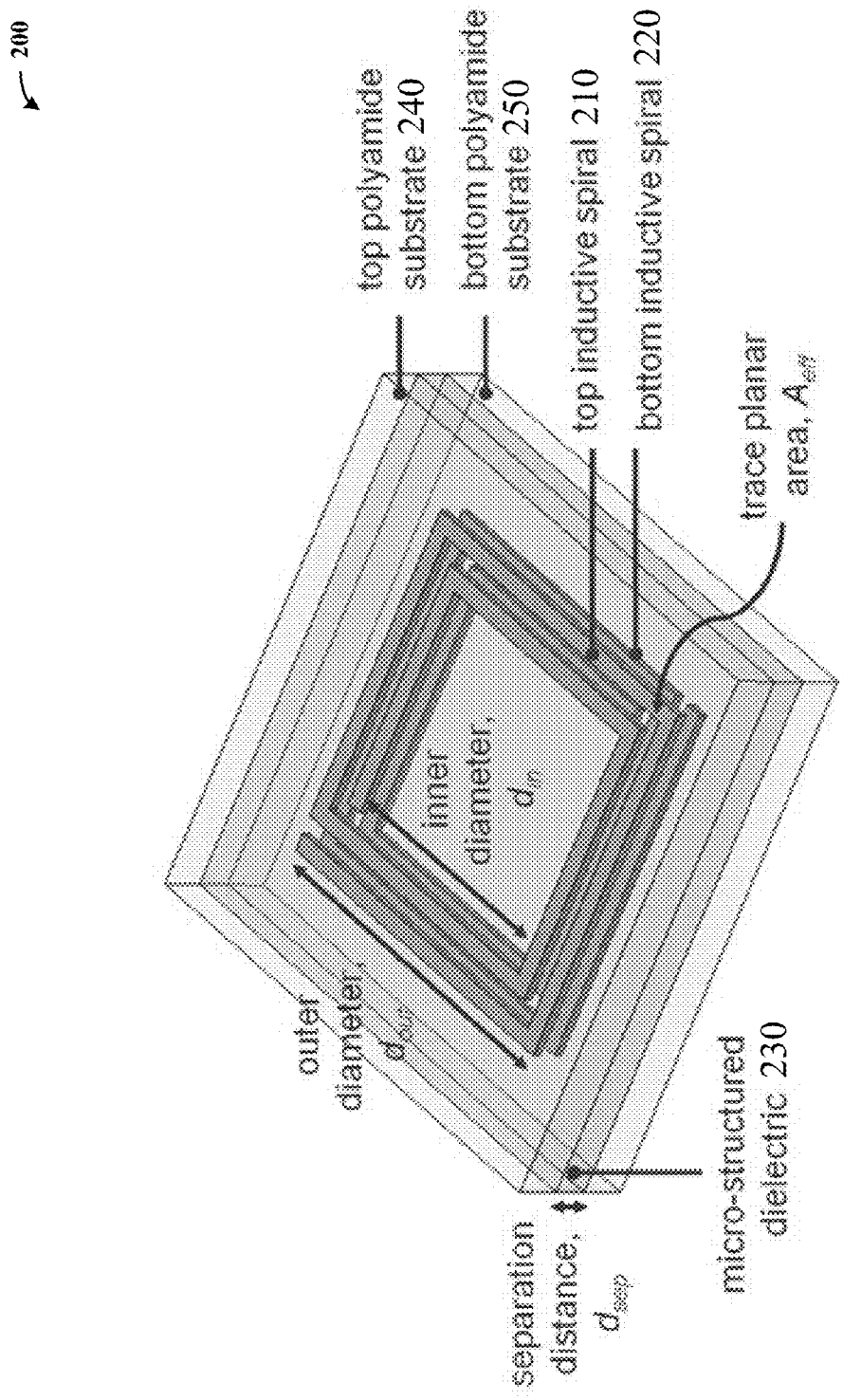
FIG. 2 shows a resonant apparatus, in accordance with another example embodiment.

FIG. 2 shows a resonant apparatus 200, in accordance with another example embodiment. The apparatus 200 includes a top inductive spiral 210 and a bottom inductive spiral 220, which are separated by a micro-structured dielectric 230. A top polyamide substrate 240 is over the micro-structured dielectric 230, and may include or otherwise secure the top inductive spiral 210 to the micro-structured dielectric. A bottom polyamide substrate 250 is below the micro-structured dielectric 230, and may include or otherwise secure the bottom inductive spiral 220 to the micro-structured dielectric. The micro-structured dielectric 230 is responsive to pressure by altering a state of compression thereof (e.g., by compressing in response to an increase in pressure, or by expanding in response to a decrease in pressure). As such, the separation distance $d_{sep}$ between the inductive spirals is altered, as is the resulting resonance thereof, based on pressure.

Aspects that set the responsiveness of the resonance to pressure include characteristics such as material and shape of the micro-structured dielectric 230, initial separation distance of the inductive spirals (e.g., at atmospheric pressure), as well as the planar area, outer/inner diameters, thickness and spacing of the inductive spiral traces. As such, device area or a number of turns can be scaled down to increase the resonant frequency. For instance, a 4×4 mm$^2$ readout antenna is inductive at low frequencies but exhibits self-resonance near 2 GHz. This self-resonance causes a magnitude peak and phase reversal in the input impedance measured at a readout antenna but produces no discernible disturbance in the PRD and GDD spectra. Hence, sensor resonant peaks can be distinguished with the PRD and GDD detection schemes at high frequencies, independent of the readout antenna design.

The effective spiral length of the inductive spirals 210 and 220 may be set to achieve desired coupling to a readout antenna in the near field. This relationship may be implemented in an analogous form to that of the number of inductor turns to mutual inductance in a transformer. As thinner and more tightly spaced spirals are fit into a given area, the effectiveness of increasing spiral length can be affected by parasitic resistances and capacitances, in view of which the characteristics are set accordingly. In some embodiments, a 0.1 mm$^3$ device is designed with 5 turns in a 1 mm$^2$ area with a minimum feature size and pitch of 25 µm, to achieve desirable operation. In some implementations, edges of the spirals are removed and a more rounded form factor is created for comfort and ease of implantation (e.g., in human pulse waveform and in vivo animal applications).

Figure 3:
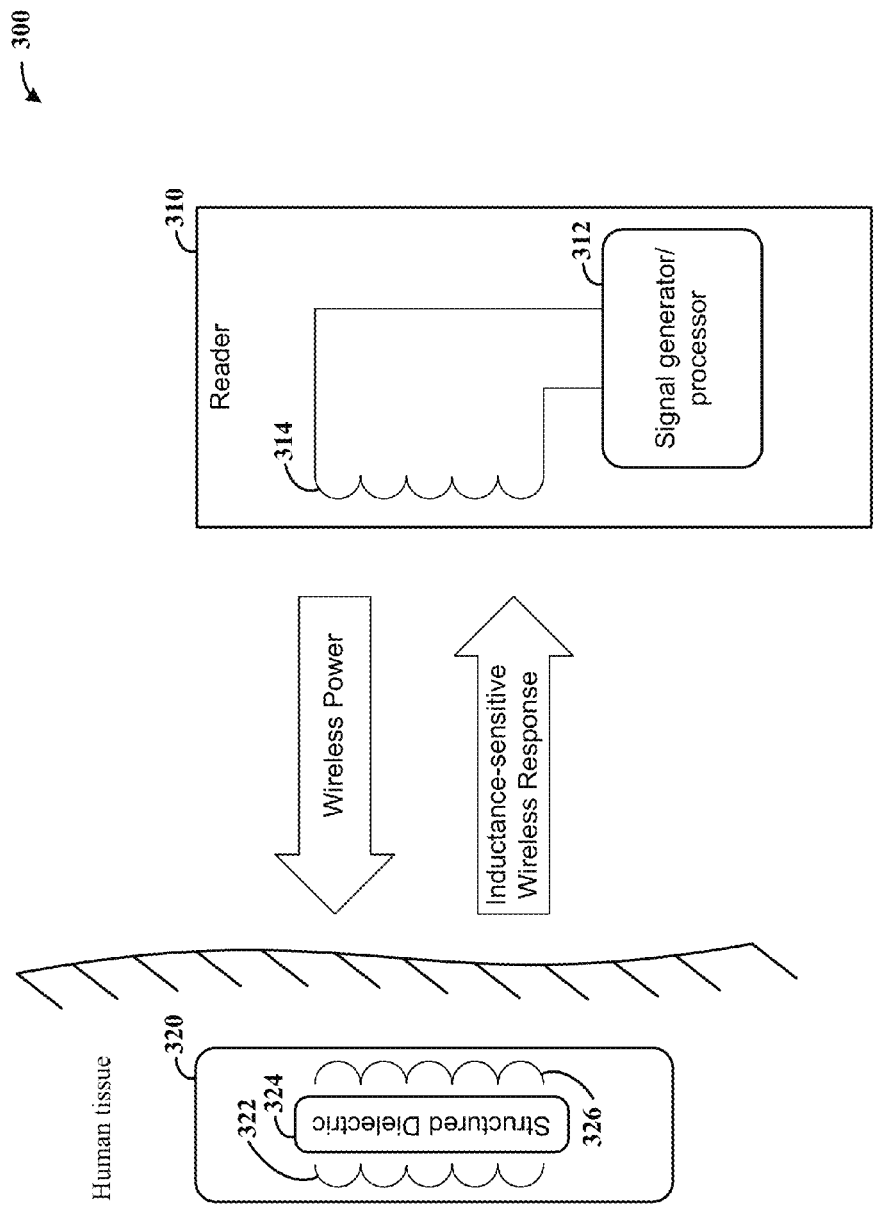
FIG. 3 shows a pressure sensor apparatus and system involving an implanted sensor, in accordance with another example embodiment.

FIG. 3 shows a pressure sensor apparatus and system 300 involving an implanted sensor 320, in accordance with another example embodiment. By way of example, the sensor 320 is depicted as being implanted within human tissue, which may involve one or more of vessels, cardiac tissue, brain tissue and others. The sensor 320 includes respective inductors 322 and 326, separated by a structured dielectric 324. The inductors 322 and 326 operate to provide resonance that is based upon a degree of compression of the structured dielectric 324, and therein providing an indication of pressure in an environment in which the sensor 320 is deployed.

The system 300 optionally includes a reader 310 that operates to both introduce wireless power (e.g., an electromagnetic field) to the sensor 320, and to read out resonance characteristics of the sensor via such a wireless field. The reader 310 includes a signal generator/processor 312 as well as an antenna circuit 314 that transmits the power to the sensor 320 and collects a response therefrom. The sensor 320 is responsive to the wireless power by interacting with a field generated by the reader 310 according to a resonance provided by the inductors 322 and 326. This interaction is sensed by the reader 310, which uses the sensed interaction to determine a pressure condition of the environment within the tissue in which the sensor 320 is implanted.

Accordingly, when the inductors 322 and 326 exhibit changes in resonance based on pressure-induced compression of the structured dielectric 324, the reader 310 detects this resonance and correlates the detected resonance to pressure. This correlation may, for example, involve determining a pressure, or determining a relative pressure (e.g., a pressure change) such as for detecting a patient's pulse in which an actual pressure value may not be needed. Where a specific pressure is sensed, the sensor may be calibrated to correlate exhibited resonance with pressure. Such a correlation may be stored (e.g., as a lookup table) and used to determine actual pressure applied to the sensor 320.

Various embodiments are directed to monitoring, such as intermittent or continuous monitoring, of internal physiological parameters of patients. One or more sensors as described herein may be implemented for real-time pressure monitoring passive, flexible, millimeter-scale sensors (e.g., sizes of 1×1×0.1 mm$^3$ or less). This level of dimensional scaling is facilitated by the sensor design, passive action and related detection schemes, which may address challenges as discussed above or otherwise relating to operating frequency limits and lossy tissue environments. For instance, such approaches may be implemented to capture human pulse waveforms wirelessly in real-time as well as to monitor in vivo ICP continuously in proof-of-concept mice studies with sensors down to 2.5×2.5×0.1 mm$^3$. Various embodiments are directed to printable wireless sensor arrays, such as with inductors characterized herein being printed, for real-time spatial pressure mapping. Using these approaches, multiple physiological parameters may be monitored for biomedical research and patient care. Other non-biological implementations may also be realized, such as for pressure monitoring in various environments, including those in which wired monitors may be challenging to implement.

As discussed above, a variety of approaches can be used to correlate frequency to pressure. In the linear region, the expression below can be used to translate peak frequency measurements $f_0$ into physical pressure values $P(f_0)$, $$P(f_0) = \frac{f_0 - f_0|_{P=0}}{\frac{df}{dP}}. \tag{8}$$

The zero pressure intercept $f_0|_{P=0}$ and pressure sensitivity $$\frac{df}{dP}$$

are derived from a linear regression of the pressure calibration curve over the 0-100 mmHg region. Using this measured calibration curve with PRD detection of the sensor resonant frequency, the same 2-turn 4×4 mm$^2$ device is monitored over 1 min. period.

In some embodiments, a human arterial pulse waveform is tracked with wireless sensors. A sensor such as a round 2.5×2.5 mm$^2$ sensor device is placed on the radial artery and secured with silicone tape. A readout antenna is placed above the wireless surface sensor, and the pressure waveform is wirelessly measured with the readout antenna in real-time.

Another embodiment is directed to pressure mapping using a plurality of sensors, such as a flexible 2×2 array of four 2×2 mm$^2$ sensors. Each pressure sensor has a unique resonant frequency (at a common pressure), and can thus be individually detected/addressed. Each sensor's nominal pressure resonant frequency can be tuned by systematically varying the spiral length as or other related characteristics as discussed herein.

Yet another embodiment is directed to detecting flow rate of fluid, using pressure differentials. For instance, sensors as described herein can be placed along a fluid path and used to monitor pressure differentials, which can be used as an indication of flow rate. Such approaches may, for example, be implemented for monitoring cerebrospinal fluid flow in shunt applications. The flow rate can be used in a feedback loop to control the shunt valve opening and closing. Each sensor can be tuned to possess an individually-addressable resonant frequency band (e.g., spaced 350 MHz apart). Each sensor may occupy a bandwidth of 100 MHz to cover the physiological pressure range of 0-100 mmHg. All sensors may, for example, be concurrently monitored with a single readout antenna. Unique resonant peaks corresponding to individual sensors in the array can be distinguished in a GDD spectrum.

Various embodiments, including experimental-type embodiments, are characterized in the underlying provisional application, and as follows. In some embodiments, electromagnetic coupling between a readout antenna and a resonant device is simulated and exported as a two-port S parameter model. Full-system modeling is achieved by co-simulation of the detection circuit in the RF/microwave circuit simulator with a coupled readout and sensor subsystem as a 2-port black box network defined by imported parameters. PRD and GDD spectrums are derived by also simulating in the absence of sensor. Sensors are made using a low-cost method of wax printing and/or standard lithography techniques. In the low-cost method, copper coating is applied to a flexible polyimide film as substrate, and a layer of wax pattern is printed onto the copper surface followed by etching in ferric chloride solution at 50° C. for about 5 min. until the non-waxed surface (exposed copper surface) is completely etched away. The wax layer is then removed by sonicating in acetone. In the lithography method, a layer of photoresist is patterned onto a polyimide coated silicon wafer, followed by thermal evaporation of 900 nm of copper, and lift-off of the photoresist layer in acetone.

In further embodiments, to obtain the elastomer microstructures, silicon mold indentations are replicated on PDMS (e.g., Sylgard® 184, available from Dow Corning of Midland, Mich.) by performing a mold-making procedure twice, first on the silicon, then on the replicated structures in PDMS, to create a soft lithographic mold identical (or nearly identical) to the silicon indentations. Next, a thermoplastic elastomer is molded to form the elastomeric microstructures by spin-coating from a tetrahydrofuran solution with a concentration of 75 mg/mL at a speed of 2000 rpm for 1 min.

In connection with some embodiments, wireless detection and monitoring is accomplished through a network analyzer connected to the 4×4 mm$^2$ readout printed antenna through a cable. The network analyzer may be controlled via USB VISA interface by a Matlab program. Triggering of excitation and capturing of reflection spectrums, spectrum signal processing, resonance detection, and GUI output can all be implemented in Matlab. For characterization measurements, input reflection spectra are averaged over 10 sweeps of 1601 frequency points and white noise is removed with a 5-point medium filter. The same number of frequency points is captured without averaging and filtering in continuous monitoring studies.

Various circuit-based building blocks and/or other modules may be implemented to carry out one or more of the operations and activities described herein or in the above-referenced provisional application, and/or shown in the block-diagram-type figures. In such contexts, these building blocks and/or modules represent circuits that carry out one or more of these or other related operations/activities. For example, in certain of the embodiments discussed above and in the provisional application, one or more blocks and/or modules are discrete logic circuits or programmable logic circuits configured and arranged for implementing these operations/activities, as in the described circuit modules/blocks. Referring to FIG. 3, various blocks as shown in the reader and related functions described in the specification may be implemented using such circuitry. In certain embodiments, the programmable circuit is one or more computer circuits programmed to execute a set (or sets) of instructions (and/or configuration data). The instructions (and/or configuration data) can be in the form of firmware or software stored in, and accessible from, a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Various embodiments described above, and discussed in the provisional application may be implemented together and/or in other manners. One or more of the items depicted in the present disclosure and in the provisional application can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. A method comprising:
providing a compressible dielectric as part of a resonant circuit having inductive conductors separated by the compressible dielectric, wherein the compressible dielectric supports the inductive conductors and is positioned between the inductive conductors, each of the inductive conductors includes a number of turns that correspond to a resonant frequency for an initial separation distance between the inductive conductors, and the compressible dielectric includes separated portions of structured dielectric material that are configured with the inductive conductors to set responsiveness of the resonant circuit to pressure;
applying an external energy field to the resonant circuit; and
using energy from the external energy field, wirelessly detecting pressure applied to the compressible dielectric by:
operating the resonant circuit in a first state in which the compressible dielectric is in a first state of compression corresponding to a first pressure applied to the compressible dielectric, and causing the resonant circuit to exhibit a first resonant frequency in response to the external energy field, the first resonant frequency being based upon the first pressure, and
operating the resonant circuit in a second state in which the compressible dielectric is in a second state of compression corresponding to a second pressure that is different than the first pressure and applied to the compressible dielectric, and causing the resonant circuit to exhibit a second resonant frequency in response to the external energy field, the second resonant frequency being based upon the second pressure and being different than the first resonant frequency, and detecting, using a reader circuit, the pressure applied to the compressible dielectric by detecting a resonant frequency of the resonant circuit via an interaction between the resonant circuit and the external energy field, wherein the resonant frequency is greater than a self-resonant frequency of the reader circuit.

2. The method of claim 1, further including implanting the resonant circuit in a live being, wherein operating the resonant circuit in the first and second states includes applying the external energy field and monitoring pressure changes within the live being by operating the resonant circuit and detecting frequency characteristics of the energy field that are responsive to the resonant frequency of the resonant circuit, and by assessing frequency characteristics in power reflection distortion spectrum or in group delay distortion spectrum, using changes in the resonant frequency as an indication of pressure changes.

3. The method of claim 1, wherein operating the resonant circuit in the first and second states includes using characteristics of the compressible dielectric to alter the resonant frequency of the inductive conductors, and wherein each resonant frequency is detected by triggering excitation over a linear sweep and a fixed frequency range, and a resultant input reflection spectrum is captured, wherein the dielectric characteristics of the compressible dielectric are altered in response to deformation of the separated portions of the dielectric material causing the dielectric material to fill in air gaps between the dielectric material with the first and second pressure applied.

4. The method of claim 1, wherein operating the resonant circuit in the first and second states includes using spiral resonators that rotate in opposite directions relative to one another and wherein the spiral resonators are configured and arranged to, in response to compression or expansion of the compressible dielectric, provide the resonant frequency exhibited in each state.

5. The method of claim 1, wherein the resonant circuit, the compressible dielectric and the inductive conductors are integrated in a sensor having a length dimension size of between 1 and 2.5 mm and at least one of the first and second resonant frequencies is on an order of GHz, and the method further including determining a characteristic of pressure applied to the compressible dielectric by detecting characteristics of an energy field affected by the resonant circuit and the resonant frequency thereof.

6. The method of claim 1, further including determining a characteristic of pressure applied to the compressible dielectric by detecting characteristics of an energy field affected by the resonant circuit and the resonant frequency thereof and wherein determining a characteristic of pressure includes detecting peak power reflection changes over a captured input frequency spectrum, and detecting a resonant frequency of the resonant circuit based on a maximum in a power reflection distortion spectrum.

7. The method of claim 1, further including determining a characteristic of pressure applied to the compressible dielectric by detecting characteristics of an energy field affected by the resonant circuit and the resonant frequency thereof and wherein determining a characteristic of pressure includes detecting a change in reflection group delay, and identifying the resonant frequency based on a maximum of group delay distortion over an input frequency range.

8. The method of claim 1, wherein providing the resonant circuit includes providing a plurality of sensors, each sensor having a different resonant frequency at a common pressure, and each sensor having a pair of inductive conductors separated by a dielectric, further including applying the sensors in different locations, and mapping pressure at the different locations by detecting respective responses of the sensors using the respective resonant frequencies to correlate each response with a specific sensor.

9. The method of claim 1,
wherein applying the external energy field to the resonant circuit includes using a remote reader circuit to apply an electromagnetic field to the resonant circuit,
wherein the resonant circuit, the compressible dielectric and the inductive conductors are integrated in a sensor that is sized with a thickness dimension of about 0.1 mm, and the method further including using the remote reader circuit to detect frequency characteristics of the resonant circuit field based on reflection of the electromagnetic field from the resonant circuit, and detecting a pressure applied to the resonant circuit based on the detected frequency characteristics.

10. An apparatus for use with a reader circuit which has a self-resonant frequency, the apparatus comprising:
a resonant circuit having inductive conductors; and
a compressible dielectric shaped to form a plurality of separated portions tapered nearer one of the inductive conductors, and configured and arranged to deform to fill in gaps within material of the compressible dielectric in response to applied pressure for increasing effective permittivity and to support the respective inductive conductors, the inductive conductors being separated by the compressible dielectric and the compressible dielectric including separated portions of the dielectric material that are configured with the inductive conductors to compress and expand in response to changes in pressure, and to operate with the inductive conductors to provide:
a first state in which the compressible dielectric is in a first state of compression corresponding to a first pressure applied to the compressible dielectric, and in which the resonant circuit exhibits a first resonant frequency in response to an external energy field, the first resonant frequency being based upon the first pressure, and
a second state in which the compressible dielectric is in a second state of compression corresponding to a second pressure that is different than the first pressure applied to the compressible dielectric, and in which the resonant circuit exhibits a second resonant frequency in response to the external energy field, the second resonant frequency being based upon the second pressure and being different than the first resonant frequency, wherein the first and second resonant frequencies are greater than the self-resonant frequency of the reader circuit.

11. The apparatus of claim 10, wherein the inductive conductors include first and second spiral resonators separated by the compressible dielectric, the spiral resonators forming a resonant tank configured and arranged to exhibit a resonant frequency that is based upon a state of compression of a portion of the compressible dielectric that separates the first and second spiral resonators.

12. The apparatus of claim 10, wherein the inductive conductors include first and second spiral resonators separated by the compressible dielectric, the spiral resonators being positioned to rotate in opposite directions relative to one another, and wherein the first and second spiral resonators are configured and arranged to provide the first and the second resonant frequencies in response to compression or expansion of the compressible dielectric.

13. The apparatus of claim 10, wherein the inductive conductors include first and second spiral resonators separated by the compressible dielectric, the spiral resonators forming a resonant tank configured and arranged to exhibit a resonant frequency that is based upon a state of compression of the compressible dielectric that corresponds to a pressure applied thereto, the resonant frequency being indicative of the applied pressure.

14. The apparatus of claim 10, wherein the resonant circuit is configured and arranged to provide an indication of pressure applied to the compressible dielectric by interacting with the external energy field, the indication being remotely detectable via the energy field.

15. The apparatus of claim 10, further including a housing structure configured and arranged to secure the compressible dielectric and the resonant circuit for passive wireless transmission of a wireless signal, responsive to changes in pressure applied to the compressible dielectric, based upon the resonant frequency of the resonant circuit.

16. The apparatus of claim 10, wherein the compressible dielectric is a microstructured dielectric having at least one undulating side.

17. The apparatus of claim 10, wherein the resonant circuit is configured and arranged to couple signals and power via the energy field using near-field electromagnetic coupling, and to use power received via the energy field to communicate a signal indicative of the resonant frequency.

18. The apparatus of claim 10, wherein the compressible dielectric is configured and arranged with the resonant circuit to exhibit an impedance change in response to compression of the compressible dielectric.

19. The apparatus of claim 10, further including the reader circuit configured and arranged to generate the external energy field, and to detect pressure applied to the compressible dielectric by detecting the resonant frequency of the resonant circuit via an interaction between the resonant circuit and the external energy field.

20. An apparatus for use with a reader circuit which has a self-resonant frequency, the apparatus comprising:
a structured elastomeric dielectric layer configured and arranged with microstructures that are separated by gap regions, the microstructures and gap regions being configured and arranged to exhibit a changed dielectric constant of the structured elastomeric dielectric layer in response to applied pressure; and
a resonant circuit including first and second inductive coils,
the first and second inductive coils being configured and arranged with a resonant frequency that varies in response to changes in the dielectric constant due to the applied pressure, the first and second inductive coils being separated by compressible dielectric material of the structured elastomeric dielectric layer and the first and second inductive coils being positioned to rotate in opposite directions relative to one another, at least one of the inductive coils being configured and arranged to receive wireless energy, and the first and second inductive coils being configured and arranged to use the wireless energy to transmit a wireless signal that is based upon the dielectric constant and indicative of the applied pressure, wherein the resonant frequency of the resonant circuit is greater than a self-resonant frequency of the reader circuit.

* * * * *